United States Patent [19]

Dury

[11] Patent Number: 5,067,898

[45] Date of Patent: Nov. 26, 1991

[54] EXTERNAL FIXING DEVICE FOR BONE SURGERY

[76] Inventor: Georges E. Dury, Avenue Franklin Roosevelt 141, 1050 Brussels, Belgium

[21] Appl. No.: 439,367

[22] PCT Filed: Apr. 28, 1988

[86] PCT No.: PCT/BE88/00012

§ 371 Date: Nov. 13, 1989

§ 102(e) Date: Nov. 13, 1989

[87] PCT Pub. No.: WO88/08691

PCT Pub. Date: Nov. 17, 1988

[30] Foreign Application Priority Data

May 14, 1987 [BE] Belgium .............................. 08700535

[51] Int. Cl.$^5$ .............................................. A61C 3/00
[52] U.S. Cl. ........................................ 433/75; 606/96
[58] Field of Search ............... 433/49, 75, 76; 606/96, 606/98

[56] References Cited

U.S. PATENT DOCUMENTS

| | | | |
|---|---|---|---|
| 3,664,022 | 5/1972 | Small | 433/75 |
| 3,760,504 | 9/1973 | Ljubarsky et al. | 32/63 |
| 3,835,849 | 9/1974 | McGuire | 606/96 |
| 3,895,444 | 7/1975 | Small | 433/75 |
| 4,257,411 | 3/1981 | Cho | 606/96 |
| 4,364,381 | 12/1982 | Sher et al. | 606/96 |
| 4,718,414 | 1/1988 | Saunders et al. | 606/96 X |
| 4,901,711 | 2/1990 | Goble et al. | 606/98 |
| 4,968,250 | 11/1990 | Small | 453/75 X |

FOREIGN PATENT DOCUMENTS

| | | | |
|---|---|---|---|
| 215765 | 1/1988 | European Pat. Off. | |
| 2907962 | 7/1980 | Fed. Rep. of Germany | 606/96 |
| 3412362 | 10/1985 | Fed. Rep. of Germany | 606/96 |
| 2412302 | 7/1979 | France | |
| 772536 | 10/1980 | U.S.S.R. | 606/96 |

*Primary Examiner*—Robert P. Swiatek
*Assistant Examiner*—Nicholas D. Lucchesi
*Attorney, Agent, or Firm*—Cushman, Darby & Cushman

[57] ABSTRACT

An external fixing device for bone surgery, particularly dento-maxillo-facial surgery, includes at least a rigid rod having a portion of constant cross-section and rectilinear axis. A spacer element, such as a lip spacer, is fixed to a rod at a distance from the extremities of the portion substantially perpendicularly to the axis of the rod portion. At least one moving element is associated to the portion to freely slide along the latter. There is provided in the moving element and opening of which the axis is substantially parallel to the axis of the rod portion, which opening provides a passage for a bone trepanation tool. An immobilizer is provided on the element to immobilize it with respect to the rod portion.

6 Claims, 5 Drawing Sheets

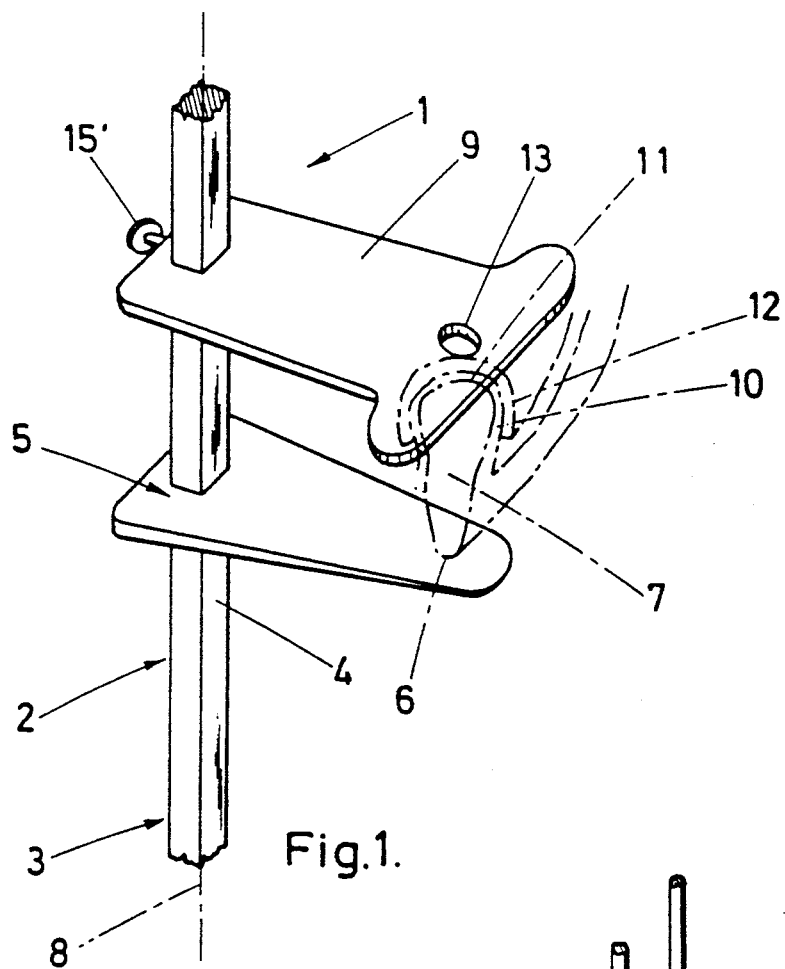
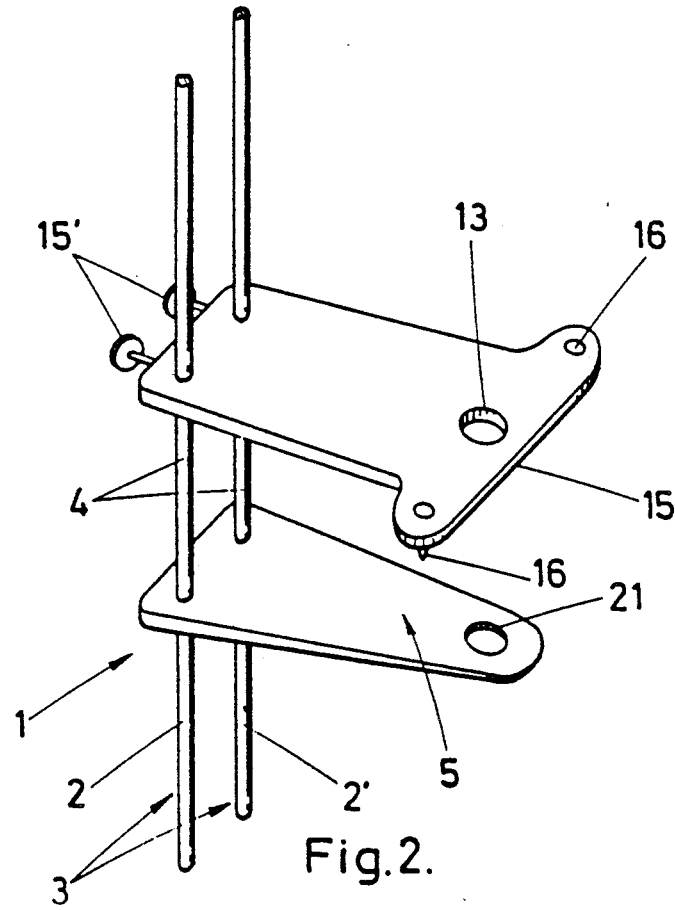

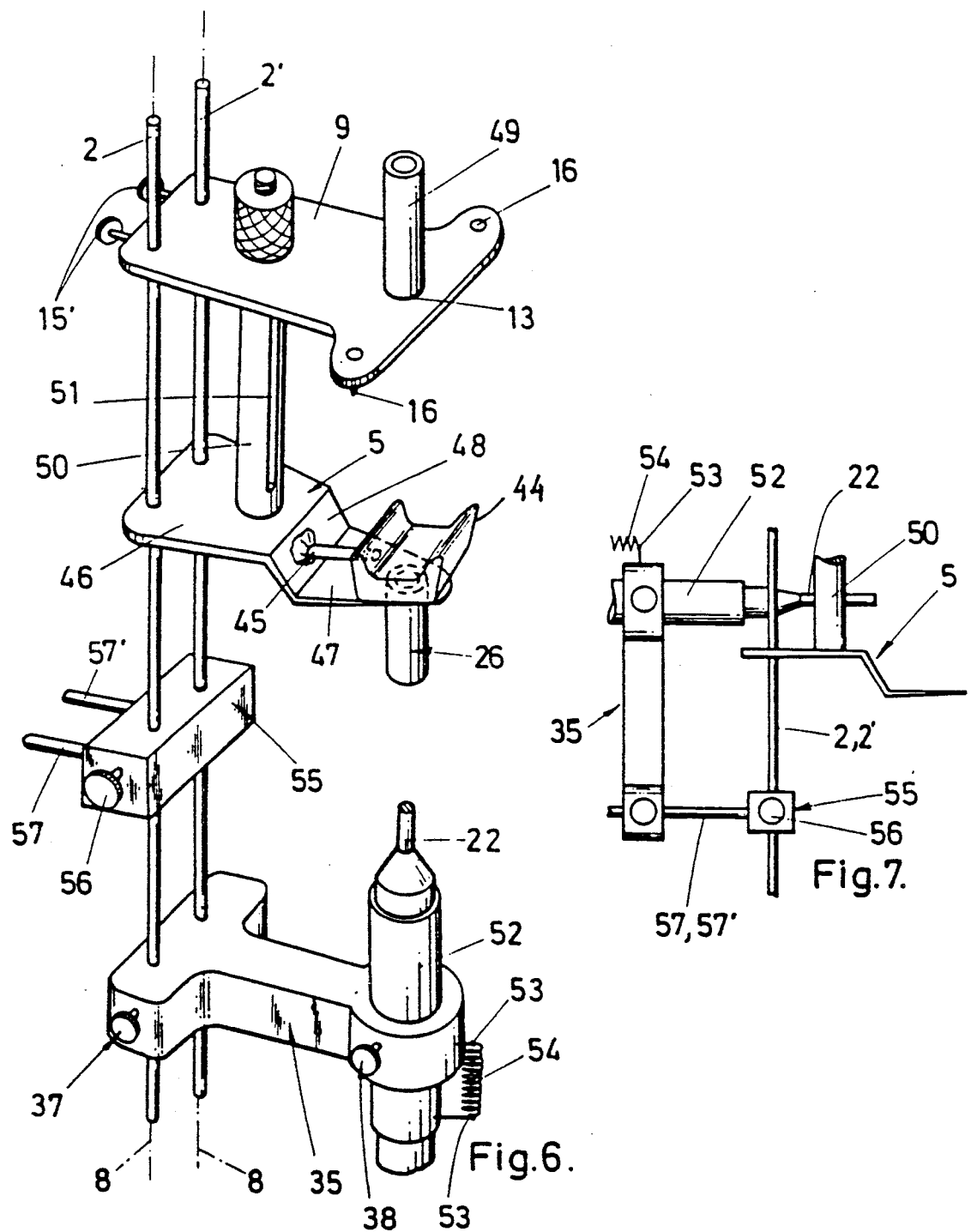

EXTERNAL FIXING DEVICE FOR BONE SURGERY

BACKGROUND OF THE INVENTION

The present invention relates to an external fixing device for bone surgery, particularly dento-maxillo-facial surgery, and especially to a device for carrying out trepanation, allowing implants to be positioned.

The invention aims to provide an external fixing device of the above-mentioned kind, which can be equipped with various fittings allowing one to carry out with a very high precision all the necessary trepanations for positioning implants whatever the kind of the latter may be.

SUMMARY OF THE INVENTION

To this end, according to the invention, this external fixing device comprises one or more undeformable rods serving, in particular, as a handle of the fixing device and presenting a portion of constant cross-section and of rectilinear axis. The device further includes a spacer element, such as a lip retractor, intended to bear on a first face of the bone to be trepaned and which is fixed to the rod at a distance from the extremities of said portion of the rod and substantially perpendicularly to the axis of said rod portion, one or more moving elements associated with the above-mentioned rod portion in order to be able to freely slide along this portion so as to rest either on the mucosa covering a second face of the bone, opposite to the first face with which the spacer element cooperates, or on a protection plate for this mucosa, or with this second face of the bone in which an opening is provided, this opening having an axis substantially parallel to the axis of the rod portion, this opening being intended to allow the passage of a tool for trepaning the bone, such as a bur. And the device further includes means provided on said element in order to immobilize it in a selected position with respect to said rod portion.

According to an embodiment of the invention, the fixing device comprises a moving support for a trepanation tool such as a bur-holder angle-shaped piece arranged to freely slide along said rod portion opposite to the spacer element with respect to the moving element, means arranged to immobilize the moving support with respect to the rod in a selected position, means for containing the bur-holder angle-shaped piece, and means for immobilizing it with respect to the moving support in order that the bur and the opening provided in the moving element are coaxial.

According to an advantageous embodiment of the invention, the external fixing device comprises a moving member provided for supporting a guide for the trepanation tool in order that this guide and the opening of the spacer element are coaxial, this member freely sliding onto the rod portion opposite to the moving element with respect to the spacer element and presenting means arranged to immobilize it on the rod portion in a selected position.

According to a particularly advantageous embodiment of the invention, the fixing device comprises, on the one hand, a moving support for a trepanation tool, such as a manual bur-holder piece, this support being arranged to freely slide along the rod portion, opposite to the spacer element with respect to the moving member, means arranged to immobilize this support in a selected position with respect to the rod portion, and means arranged to immobilize the trepanation tool in order that its axis coincides with the axis of the opening of the spacer element. The fixing device of this embodiment further includes a moving support for one or more trepanation tools, such as a bur, this support being arranged to freely slide along the rod portion in the portion of the latter, which is comprised between the spacer element and the moving element, means arranged to immobilize the support in a selected position with respect to the rod portion and means for immobilizing the trepanation tool in the support in order that its axis is transverse to the axis of the opening existing in the spacer element.

BRIEF DESCRIPTION OF THE DRAWINGS

Other details and particularities of the invention will become apparent from the description and the accompanying drawings which show, by way of non-limitative examples, some particular embodiments of the external fixing device according to the invention.

In the drawings

FIG. 1 is a partly broken away perspective view showing the external fixing device according to the invention in its simplest embodiment.

FIG. 2 is a partly broken away perspective view showing a variant of the external fixing device of FIG. 1.

FIG. 6 is a perspective view showing a variant of the external fixing device shown in FIGS. 3 to 5.

FIG. 7 is a fragmentary elevation view showing another arrangement of the fixing device shown in FIG. 6.

In the different figures, the same reference numerals relate to identical or analogous elements.

DETAILED DESCRIPTION

Figure 3:
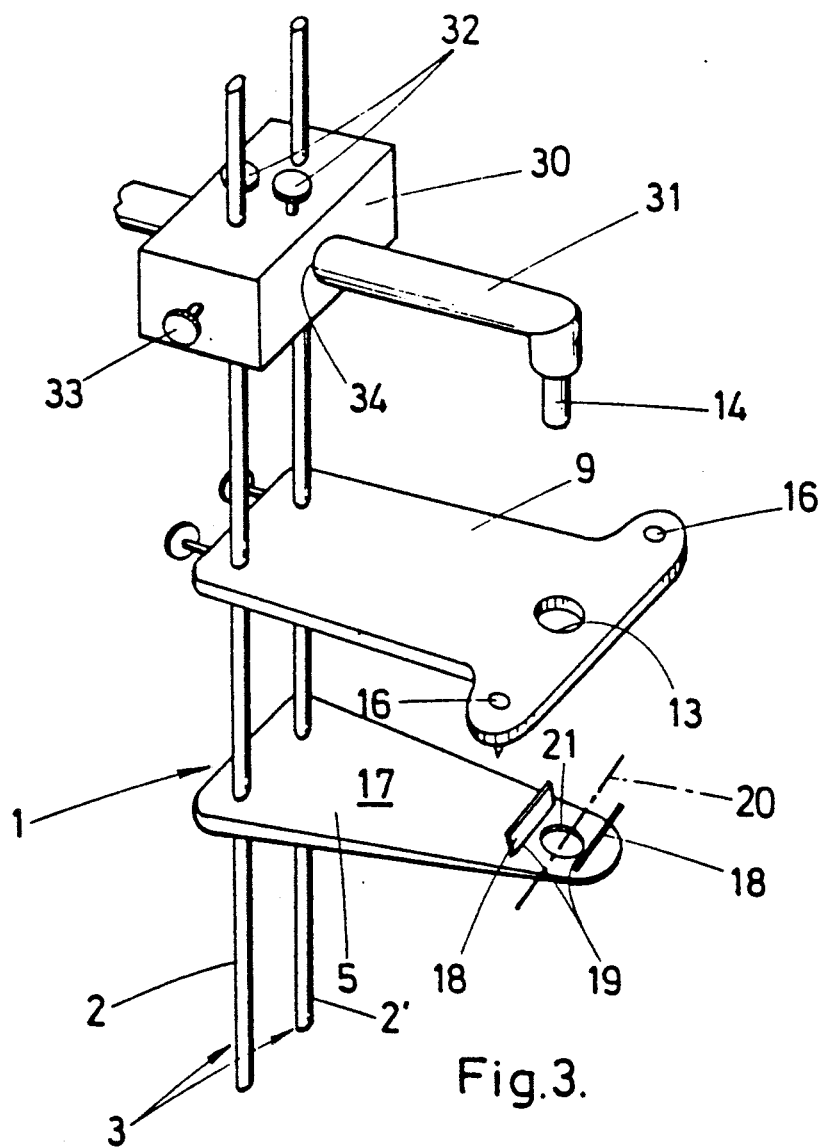
FIGS. 3 to 5 are views analogous to FIG. 2, showing as a partly broken away view, on the one hand, the external fixing device equipped with various fittings and, on the other hand, details of constituent elements of the fixing device.

The external fixing device 1 according to the invention and such as shown in the drawings is more particularly intended to allow trepanations to be made easily and in an extremely precise manner in dento-maxillo-facial surgery in order to position implants.

In its most simplified embodiment, such as is shown in FIGS. 1 and 2, the external fixing device 1 comprises, for example, for positioning single implants of the rod type, either one undeformable rod 2 (FIG. 1) or two parallel undeformable rods 2 and 2' (FIG. 2), the end 3 of which can, in particular serve as a handle of the fixing device and which each present a portion 4 of constant and rectilinear cross-section. On this portion 4 of the rod 2 or of the rods 2 and 2', a spacer element such as a lip spacer 5 is fixed at a distance from the extremities of said portion 4, which spacer element is intended to bear on a first face 6 of the bone to be trepaned 7, the latter being schematically shown in dot-and-dash line on FIG. 1, the spacer element extending substantially perpendicularly to the axis 8 of the rod portion 4. This rod also bears a moving element 9 which freely slides along the axis 8 to rest either on the mucosa covering the face 11 of the bone opposite to the face 6 or on a protection plate 12 for the mucosa, such as shown in dot-and-dash line in FIG. 1, or on the face 11 of the bone. This element 9 is provided with an opening 13 of which the axis is parallel to the axis 8 and which allows the passage of a trepanation tool 14 (FIG. 3), such as a bur, and with one or more set screws 15' provided to immobilize this element 9 in a selected position with respect to the portion 4 of the rod 2 or of parallel rods 2 and 2'.

In the external fixing device shown in FIG. 1, the portion 4 of the rod 2 and the opening 13 provided in the moving element 9 have such a cross-section that the element 9 is motionless in rotation around the axis 8 of the portion 4 of the rod 2. This element 9 is advantageously arranged on the portion 4 of the rod 2 in a removable manner in order that the element can be replaced by another element 9 which is more appropriate to the trepanation to be made.

In the embodiment of the external fixing device 1 shown in FIG. 2, the moving element 9 presents on its face 15 turned to the spacer element 5, some studs 16 the points of which are intended to penetrate either into the bone 5 (FIG. 1), or into the plate 12 protecting the mucosa 10 (FIG. 1) in order to substantially immobilize the element 9 and accordingly the external fixing device 1 with respect to said bone 7 or to the protection plate 12.

As shown in FIG. 3, the spacer element 5 advantageously comprises on its face 17 turned to the moving element 9 and still to reinforce the immobilization of the fixing device 1 with respect to the bone 7, two fixed plates 18 fitting together with the spacer element 5 along two lines 19 which are substantially parallel to the plane passing through the axis of the rods 2 and 2' and regularly diverging from one another with respect to a tracing plane 20 which is parallel to the plane passing through the axes of said rods, these plates 18 resting on the bone 7 on both sides of the face 6 of the latter, with which the spacer element 5 cooperates.

Figure 4:
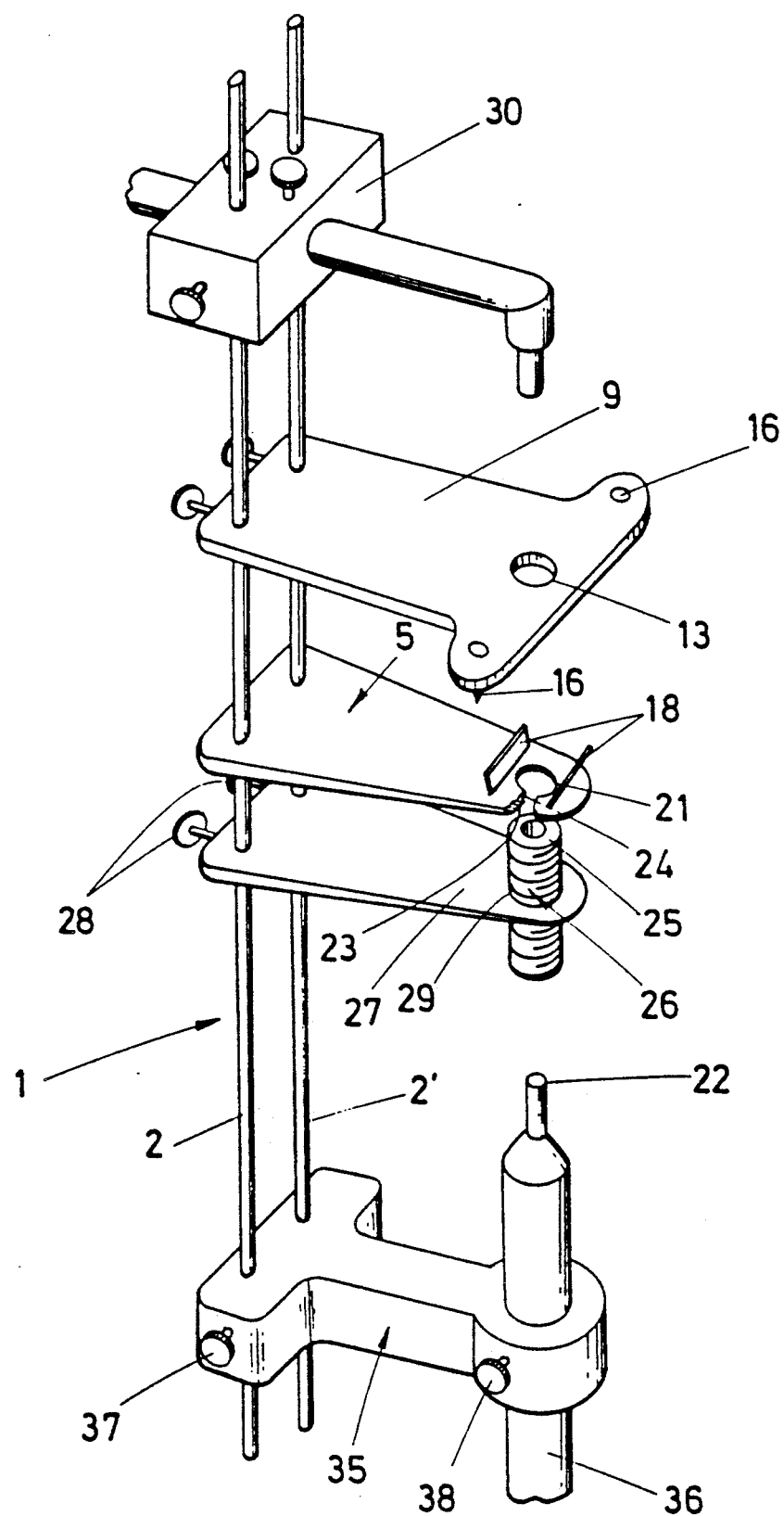
Figure 5:
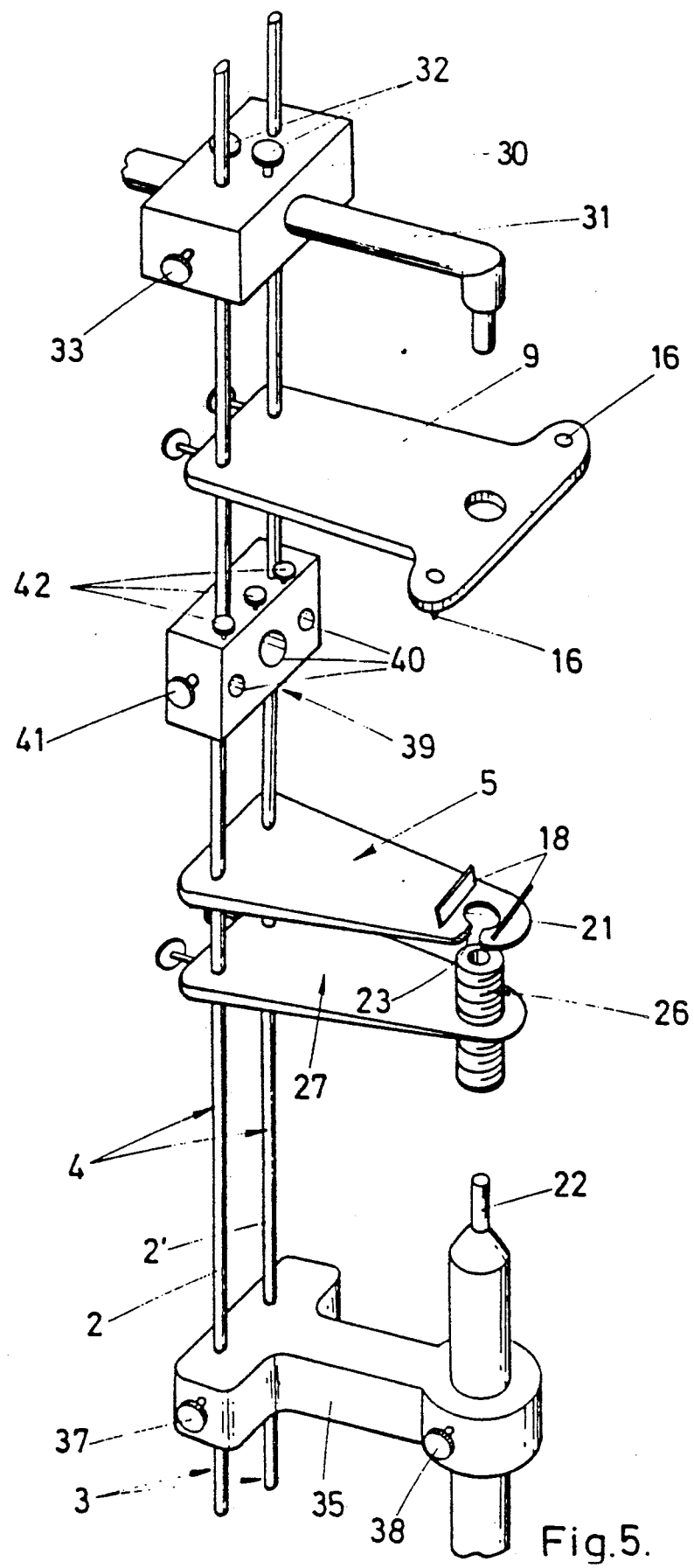

Also as shown as well by FIG. 3 as by FIGS. 2, 4 and 5, in order to allow the precise positioning of implants, necessitating trepanation of the bone 7 from faces 6 and 11 of the latter, the spacer element 5 has an opening 21 which is coaxial with the opening 13 of the moving element 9, this opening 21 allowing the passage of a trepanation tool such as the bur 22 (see FIG. 4).

In order to ensure a perfect guiding of the bur or trepan 22 when the latter is driven manually, the spacer element 5 comprises, from its face 23 (FIG. 4), a cavity 24 which is coaxial to its opening and arranged in order to receive, so as to immobilize it, the extremity 25 of a guide 26 coaxial to same opening 21 and through which the bur 22 passes. This guide 26 is advantageously supported, as shown in FIGS. 4 and 5, by means of a moving member 27 which freely slides onto the portion 4 of the rods 2 and 2', opposite to the moving element 9 with respect to the spacer element 5, set screws 28 being provided to immobilize this member 27 with respect to the rods 2 and 2' when the extremity 25 of the guide 26 is located in the cavity 23 provided in the spacer element 5. This guide 26 is arranged on the moving member 27 so that its position is controllable along a direction parallel to the axis of the portion 4 of the rods 2 and 2' and is advantageously comprised of a tube into which the bur or trepan 22 is inserted so that its axis coincides with the axis of the tube, the latter being threaded externally and cooperating with a threaded hole 29 which is provided in the member 27 and is coaxial to the openings 13 and 21, the precise control of the guide 26 with respect to the member 27 being made by rotating the threaded tube forming this guide around its axis, the threads of the tube and of the threaded hole being such that the tube remains motionless in rotation around its axis as long as it is not positively controlled in rotation.

In order that the bur or trepan 14 is perfectly guided through the opening 13 of the moving element 9, the external fixing device 1 comprises, as shown by FIGS. 3 to 5, a moving support 30 for the tool 14 which is borne by a bur-holder angle-shaped piece 31 which is arranged to freely slide along portions 4 of rods 2 and 2', opposite to the spacer element 5 with respect to the moving element 9. Set screws 32 and 33 are provided, on the one hand, for immobilizing the bur-holder angle-shaped piece 31 in the cavity 34 of the support 30 so that the bur or trepan 14 and the opening 13 of the moving element 9 are coaxial and, on the other hand, for immobilizing, when desired, the support 30 in a selected position with respect to the rods 2.

When it is desired to mechanically guide the bur or trepan 22, one can provide on the fixing device 1, as shown in FIGS. 4 and 5, a moving support 35 for a manual bur-holder piece 36 which is arranged to freely slide along the rods 2 and 2', opposite to the spacer element 5 with respect to the moving member 27. Set screws 37 and 38 are provided in order to immobilize, when desired and in a selected position, the moving support 35 with respect to the rods 2 and 2' and to immobilize the manual piece 36 so that the bur or trepan 22 has its axis coinciding with the axis of the opening 21 provided in the spacer element 5 and with the axis of the guide 26.

In order to allow a precise positioning of implants with cross-locking or of transverse fixing screws of the external fixing device cooperating with the bone, the external fixing device 1 advantageously comprises, as shown in FIG. 5, a moving support 39 having openings 40 for burs or trepans (not shown), the axes of which are parallel and located in a plane which is perpendicular to the axes of the rods 2 and 2'. The trepans guided in the openings 40 allow to carry out some trepanations which, when the openings are joined together, allow to position bladed elements which immobilize the implants. The support 39 which is arranged between the elements 5 and 9, bears set screws 41 and 42 allowing one on the one hand, to immobilize the support in a selected position with respect to the rods 2 and 2' and, on the other hand, to immobilize, when desired, the trepans in the openings 40.

Except for the spacer element 5, which is fixed to the rods 2 and 2', all the other elements 9, 27, 30, 35 and 39 are advantageously removably assembled to rods 2 and 2', so that they can be used together or separately according to the trepanations to be carried out.

The external fixing device according to the invention and shown in FIGS. 6 and 7 is more particularly a variant of the fixing device of FIG. 5, but from which the moving member 27 has been omitted. In some cases, this member can constitute a constraint for the lips retraction, and wherein the moving support 39 has been replaced by a moving support 55 intended to receive the support 35 of the trepan or of the bur 22, in order to carry out trepanations along a direction perpendicular or transverse to the plane passing by the axes of the rods 2 and 2'.

In this latter embodiment, the spacer element 5, in order to improve its insertion with respect to the bone 7, is bent and made of two parts 46, 47, which are substantially planar and substantially perpendicular to the axes 8 of the rods 2 and 2', these parts being united by a slanting section 48, the part 47 which is the most remote from the axes 8 and is intended to be located in front of the bone, being located at a lower level than the part 46. This part 47 is arranged to support a moulding 44 of the bone portion on which the spacer element must bear, such as the moulding made from information obtained by means of a scanner. Fixing means 45 for this moulding, which is removable and different for each case of trepanation, are arranged so that this moulding can follow the bone portion it reproduces so as to totally immobilize the external fixing device with respect to the bone when the latter is pinched between the moulding fixed to the spacer element 5 and the above-mentioned moving element 9. In such a case, any risk of inopportune movement of the fixing device during a trepanation is prevented.

So as to precisely guide the trepanation tool, the guide 26 which was fixed to this member 27 in the embodiment of FIG. 5, is threaded and directly fixed on the spacer element 5 in the opening 21 which is internally threaded.

In order to precisely guide a tool, analogous to the above-mentioned tool 31, the opening 13 of the moving element 9 is also advantageously provided with a tubular guide 49 which is coaxial to said opening 13, the threaded end of which is screwed into said opening 13 which is internally threaded.

So as to allow the external fixing device to be completely immobilized with respect to the bone, this device comprises a binding piece 50 arranged between the spacer element 5 and the moving element 9. This piece is parallel to the axis 8 of rods 2 and 2' and is arranged so as to allow, on the one hand, the control of the spacing between the spacer element 5 and the moving element 9 and, on the other hand, the total immobilization of both of these elements on the bone.

The binding piece 50 comprises an elongated hole 51 which is parallel to the above-mentioned axes 8 and which is intended to form a passage, for example, for the trepanation tool 22, as hereinafter explained.

The moving support 35 of this external fixing device bearing the trepanation tool 22 comprises a sleeve 52 arranged to receive and immobilize the tool 22, this sleeve freely sliding into the moving support, means 38 being provided on the latter and arranged to allow this immobilization of the sleeve 52 with respect to the moving support 35 when the fixing device is handled and transported.

The moving support 35 and the sleeve 52 each advantageously present a fixing lug 53 for one end of an interchangeable spring 54 the axis of which is substantially parallel to the axis of the sleeve, this spring which is selected according to the characteristics of the bone, allowing the sleeve to automatically progress into the support 35 for the trepanation.

This external fixing device also comprises a moving support 55 arranged to freely slide along the rods 2 and 2' near the spacer element 5 opposite to the moving element 9. Means 56 are arranged to immobilize the support 55 on the rods 2 and 2' in a selected position. Two bars 57 and 57', analogous to rods 2 and 2', are fixed to the support 55 perpendicularly to the latter. On these bars 57 and 57', the moving support 35 for a trepanation tool can be slid and be immobilized, as shown by FIG. 7, when the tool is used for a trepanation through the above-mentioned elongated hole.

It is to be understood that the invention is in no way limited to the described embodiments and that many changes can be made thereto without departing from the scope of the present patent.

I claim:

1. An external fixing device for carrying out trepanations allowing implants to be positioned during dentomaxillo-facial bone surgery,
said device comprising:
at least one rigid rod having an extremity serving as a handle for said device; each said at least one rod having a respective longitudinally extensive portion having a constant transverse cross-sectional size and shape and a longitudinal axis;
a spacer element fixed to each said at least one rod at a given distance from the respective said extremity, extending substantially perpendicularly to said longitudinal axis and arranged to bear upon a first face of a bone which is to be trepanned;
at least one movable element axially slidably mounted on said portion of each said at least one rod so as to be positionable to bear upon an opposite, second face of said bone;
means defining an opening through said at least one movable element, along an axis that is substantially parallel to said longitudinal axis, said opening being arranged to allow passage therethrough of a portion of a trepanation tool for accessing said bone; and
means for selectively immobilizing said at least one movable element to said portion of each said at least one rod at a selected position relative to said spacer element;
a movable support for a trepanation tool, said movable support being axially slidably mounted on said portion of each said at least one rod on an axially opposite side of said at least one movable element from said spacer element;
means for securing to said movable support a trepanation tool having a head coaxially aligned with said axis of said opening through said at least one movable element; and
means for selectively immobilizing said movable support to said portion of each said at least one rod at a selected position relative to said at least one movable element.

2. The device of claim 1, further comprising:
a further movable support for at least one trepanation tool axially slidably mounted on said portion of each said rod axially between said spacer element and said at least one movable element;
means for selectively immobilizing said further movable support to said portion of each said at least one rod at a selected position;
means for immobilizing at least one further trepanation tool in said further movable support with a head of the further trepanation tool aligned on an axis which is transverse to said longitudinal axis; and
said at least one rigid rod is constituted by two parallel rigid rods.

3. An external fixing device for carrying out trepanations allowing implants to be positioned during dentomaxillo-facial bone surgery,
said device comprising:
at least one rigid rod having an extremity serving as a handle for said device; each said at least one rod having a respective longitudinally extensive portion having a constant transverse cross-sectional size and shape and a longitudinal axis;

a spacer element fixed to each said at least one rod at a given distance from the respective said extremity, extending substantially perpendicularly to said longitudinal axis and arranged to bear upon a first face of a bone which is to be trepanned;

at least one movable element axially slidably mounted on said portion of each said at least one rod so as to be positionable to bear upon an opposite, second face of said bone;

means defining an opening through said at least one movable element, along an axis that is substantially parallel to said longitudinal axis, said opening being arranged to allow passage therethrough of a portion of a trepanation tool for accessing said bone; and means for selectively immobilizing said at least one movable element to said portion of each said at least one rod at a selected position relative to said spacer element; each said at least one rod being generally vertically oriented;

said spacer element comprising a first generally horizontal part located nearest said at least one rod; a second generally horizontal part located further from each said at least one rod and at a lower level than said first part, and a slanting section sloping from said first part down to said second part and joining said first part to said second part;

means defining an opening through said spacer element coaxially with said opening through said at least one movable element;

a movable member for supporting a guide, said movable member being axially slidably mounted on said portion of each said at least one rod on an axially opposite side of said spacer element from said at least one movable element;

a trepanation tool guide mounted on said movable member, said tool guide being coaxial with said opening through said at least one movable element;

means for selectively immobilizing said movable member to said portion of each said at least one rod at a selected position;

a second movable support for a trepanation tool, said second movable support being axially slidably mounted on said portion of said at least one rod on an axially opposite side of said at least one movable element from said spacer element;

means for selectively immobilizing said second movable support to said portion of said at least one rod at a selected position; and means for securing to said second movable support a second trepanation tool having a head coaxially aligned with said axis of said opening through said at least one movable element.

4. The device of claim 3, wherein:

said second movable support comprises a tubular barrel; a tubular sleeve arranged to receive and immobilize said second trepanation tool; and said means for securing said second trepanation tool to said second movable support comprises means for securing said sleeve in said tubular barrel.

5. The device of claim 4, further comprising:

a first fixing lug secured on said barrel;

a second fixing lug secured on said tubular sleeve;

a spring secured to said fixing lugs and acting parallel to said longitudinal axis in a sense to tend to axially move said sleeve towards said at least one movable member for supporting a guide.

6. An external fixing device for carrying out trepanations allowing implants to be positioned during dento-maxillo-facial bone surgery, said device comprising:

at least one rigid rod having an extremity serving as a handle for said device; each said at least one rod having a respective longitudinally extensive portion having a constant transverse cross-sectional size and shape and a longitudinal axis;

a spacer element fixed to each said at least one rod at a given distance from the respective said extremity, extending substantially perpendicularly to said longitudinal axis and arranged to bear upon a first face of a bone which is to be trepanned;

at least one movable element axially slidably mounted on said portion of each said at least one rod so as to be positionable to bear upon an opposite, second face of said bone;

means defining an opening through said at least one movable element, along an axis that is substantially parallel to said longitudinal axis, said opening being arranged to allow passage therethrough of a portion of a trepanation tool for accessing said bone; and means for selectively immobilizing said at least one movable element to said portion of each said at least one rod at a selected position relative to said spacer element;

a movable support for bar means, said movable support for bar means being axially slidably mounted on said portion of said rod on an axially opposite side of said spacer element from said at least one movable element;

means for selectively immobilizing said movable support for bar means to said portion of each said at least one rod at a selected position;

at least one bar secured to said movable support for bar means; each said at least one bar extending generally perpendicularly to said portion of each said at least one rod and constructed to accommodate a further movable support for a further trepanation tool.

* * * * *